United States Patent [19]

Jones

[11] Patent Number: 4,506,030

[45] Date of Patent: Mar. 19, 1985

[54] CATALYSTS FOR HYDROGENATION OF AROMATIC COMPOUNDS

[75] Inventor: Richard A. Jones, Austin, Tex.

[73] Assignee: The Board of Regents, University of Texas System, Austin, Tex.

[21] Appl. No.: 581,422

[22] Filed: Feb. 17, 1984

[51] Int. Cl.³ .............................................. C07F 4/02
[52] U.S. Cl. ................................ 502/155; 260/429 R; 260/429 CY; 260/439 R; 260/439 CY; 502/159; 502/160; 502/161; 502/166; 585/269
[58] Field of Search ...................... 585/266, 269, 270; 502/155, 159, 160, 161, 166; 260/429 R, 429 CY, 439 CY, 439 R

[56] References Cited

U.S. PATENT DOCUMENTS

| | | | |
|---|---|---|---|
| 3,742,071 | 6/1973 | Holmes et al. | 502/161 |
| 3,859,319 | 1/1975 | Mrowca | 260/410.6 |
| 3,900,557 | 8/1975 | Strathdee | 502/159 |
| 3,957,827 | 5/1976 | Lyons | 502/161 |
| 3,998,864 | 12/1976 | Trevillyan | 502/159 |
| 4,077,906 | 3/1978 | Hughes | 502/159 |
| 4,120,882 | 10/1978 | Wilke et al. | 502/155 |
| 4,183,825 | 1/1980 | Carlock | 502/159 |
| 4,201,728 | 5/1980 | Hughes | 502/161 |
| 4,221,744 | 9/1980 | Umreh | 502/162 |
| 4,257,972 | 3/1981 | Vidal et al. | 260/429 R |
| 4,258,206 | 3/1981 | Pittman, Jr. et al. | 502/159 |
| 4,321,414 | 3/1982 | Costa | 568/862 |
| 4,361,497 | 11/1982 | Boldt et al. | 502/159 |
| 4,434,302 | 2/1984 | De Munck et al. | 502/159 |

FOREIGN PATENT DOCUMENTS

| | | | |
|---|---|---|---|
| 978926 | 12/1975 | Canada | 502/159 |
| 0032455 | 7/1981 | European Pat. Off. | 502/159 |
| 0040891 | 12/1981 | European Pat. Off. | 502/159 |
| 2016006 | 9/1979 | United Kingdom | 502/155 |

Primary Examiner—Delbert E. Gantz
Assistant Examiner—A. Pal
Attorney, Agent, or Firm—Arnold, White & Durkee

[57] ABSTRACT

A novel transition metal catalyst which has a phosphido-type linkage is much less subject to metal loss during operations because of its greater bond strength. This catalyst will hydrogenate unsaturated hydrocarbons under milder conditions than most prior art catalysts.

15 Claims, No Drawings

CATALYSTS FOR HYDROGENATION OF AROMATIC COMPOUNDS

BACKGROUND OF THE INVENTION

The present invention relates to catalysts, and more specifically, to transition metal catalysts useful for hydrogenation reactions.

Transition metal catalysts are well-known in the prior art. Some of these catalysts have been synthesized and used in heterogeneous form. For example, the transition metal complex can be attached to a polymeric support by a linking agent. Heterogeneous catalysts have the advantage of facilitating or eliminating the catalyst recovery operations that are necessary when homogeneous catalysts are used, while retaining the advantages of high activity, selectivity, and reproduceability under mild temperatures and pressures.

The catalysts of particular interest here have transition metal complexes bonded to a polymeric support by a phosphorus containing group. Apparently all catalysts of this type used in the past have had a dative bond between the phosphorus atom and transition metal. This can be illustrated by a typical synthesis of such a compound.

The synthesis below begins with a chloromethylated styrene-divinylbenzene copolymer (1) and lithium diphenylphosphine (2).

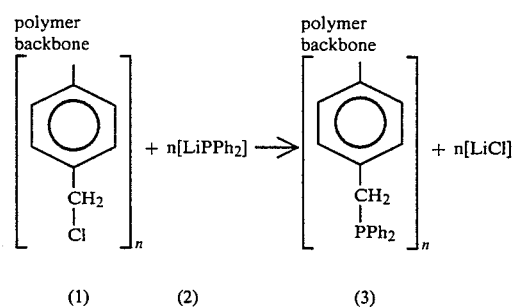

The resulting polymer supported phosphine (3) contains PPh$_2$ units which can then be attached to various transition metals, such as rhodium.

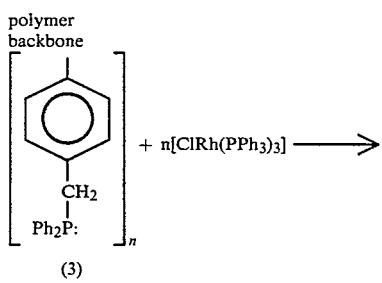

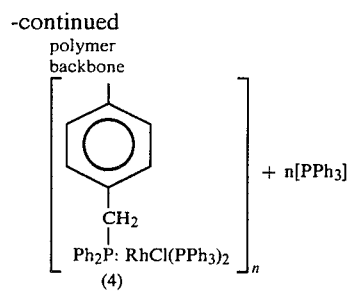

A triphenylphosphine group is lost from ClRh(PPh$_3$)$_3$ and the resulting polymeric material (4) is a catalyst with many applications.

The catalyst described above has a costly disadvantage: the dative two electron bond between the phosphorus and the rhodium is fairly weak. When such a catalyst is used in the harsh environment of commercial operations, a significant amount of rhodium will be lost from the polymeric support. Rhodium and several other transition metals commonly used as catalysts are extremely expensive, so their loss during operations can make otherwise satisfactory catalytic processes economically unfeasible.

Furthermore, prior art catalysts generally require high temperatures and pressures for the hydrogenation of aromatic hydrocarbons. Fifty atmospheres and 150° C. are not uncommon requirements, and some catalysts and reactants require even harsher conditions.

A catalyst less vulnerable to transition metal loss will provide a significant advantage in commercial operations. The same is true of one that could hydrogenate unsaturated hydrocarbons under milder conditions.

SUMMARY OF THE INVENTION

A catalyst in accordance with the present invention has the formula

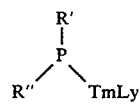

where
- R' and R" are independently any organic or inorganic functionality capable of bonding to phosphorus, such as aliphatic, alicyclic, or aromatic radicals;
- Tm is d-block transition metal; and
- Ly is any functionality capable of bonding to a d-block transition metal, such as a halide, aliphatic, alicyclic, aromatic, phosphine, phosphate, phosphite, amine, thiol, sulfide, sulfate, or sulfite radical. Alkenes and carbon monoxide are two more specific examples.

In this specification and the claims that follow, "d-block transition metal" is used to mean titanium, vanadium, chromium, manganese, iron, cobalt, nickel, zirconium, niobium, molybdenum, technetium, ruthenium, rhodium, palladium, hafnium, tantalum, tungsten, rhenium, osmium, iridium, and platinum. Iron, cobalt, nickel, ruthenium, rhodium, palladium, osmium, iridium, and platinum are transition metals that have proven especially useful for catalyst purposes.

The exact nature of the ligand Ly is not critical, so it can be a variety of groups such as those shown above, but not necessarily restricted to those examples. The same is true of the substituents R' and R".

In a catalyst in accordance with the present invention, the transition metal is attached to the phosphorus atom by a phosphido type linkage, not a dative bond as in prior art catalysts. The phosphido type linkage holds the transition metal much more firmly. Therefore, catalysts in accordance with the present invention have the potential to achieve tremendous savings by reducing catalyst losses.

Such a catalyst can be synthesized by the following steps:

R"PH$_2$ + R"M → MPR"H + R"H

R'X + MPR"H → R'PR"H + MX

R'PR"H + R"M → R'PR"M + R"H

R'PR"M + XTmLy → R'R"P—TmLy + MX where
R', R", Tm, and Ly are as stated above, and
M is a metal which is more electropositive than d-block transition metals, such as an alkali metal or an alkaline earth,
R" is an organic radical, such as n-butyl, methyl, or phenyl, and
X is any inorganic, anionic functional group, such as a halogen.

Catalysts in accordance with the present invention can be used to hydrogenate aromatic hydrocarbons under elevated temperature and pressure, although the pressure and temperature will usually be lower than prior art catalysts have generally required. Suitable temperatures will generally be less than about 100° C. and suitable pressures less than about 5 atmospheres. Since processes employing lower temperature and pressure require less energy, this feature of catalysts in accordance with the present invention can also generate substantial savings.

Catalysts in accordance with the present invention will also hydrogenate alkenes and acetylenes, and will hydroformylate alkenes.

DETAILED DESCRIPTION OF THE INVENTION

Catalysts in accordance with the present invention have the general formula

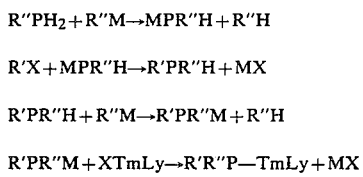

R' can be a wide variety of things, but is preferably a polymer with multiple sites (n) available for the anchoring of metal complexes via phosphorus. When such a polymer is reacted as described below with certain metallated phosphines and transition metal complexes, the end product will be a polymer supported catalyst with transition metals bound to it via phosphido-type linkages.

R" can be a wide variety of substituents, but is preferably an alkyl or aryl hydrocarbon. Phenyl and tertiary butyl groups are two specific examples.

The R" group used in synthesizing these catalysts can be any organic radical, but is preferably alkyl or aryl hydrocarbon groups, such as n-butyl or methyl.

The ligand Ly can be nearly anything that will properly complex with the transition metal, and a group of possibilities has been listed already. Norbornadiene, 1,5-cyclooctadiene, cyclopentadienes, trialkyl or triaryl phosphines, and trialkyl or triaryl phosphites are other specific examples.

The following examples illustrate specific syntheses of catalysts in accordance with the present invention, and use of such catalysts in hydrogenation reactions.

EXAMPLE 1

This synthesis began with a primary phosphine containing a single tertiary butyl group [H$_2$P(t—Bu)]. It was prepared by an acid catalyzed addition of a P—H bond to an alkene as described by Hoff and Hill [Journal of Organic Chemistry (1959), 24, 356–359, "Acid Catalyzed Additions of Phosphines to Olefins"].

This primary phosphine is a volatile liquid, having a boiling point at 760 mm Hg of 56° C., a density of 0.736 g/ml, and a molecular weight of 90. Since it is air sensitive, all manipulations of it and the other compounds used in this reaction were conducted under a nitrogen atmosphere.

Ninety hundredths of a gram (1.22 ml; 10 mmols) of H$_2$P(t—Bu) were added through a syringe to a stirred flask containing 100 ml of dry and degassed tetrahydrofuran (THF). This solution was then cooled to −100° C., and one equivalent of n-butyllithium in hexane (3.3 ml of a 3.0M solution; 10 mmols) was added through a syringe.

The reaction mixture was stirred for 6 hours while the temperature was slowly raised to room temperature. During this period, the phosphine precipitated at the lower temperatures and then redissolved as the temperature rose. The precipitate appeared completely redissolved at about −30° C.

The product of this reaction was a metallated primary phosphine having the empirical formula

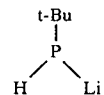

A stoichiometric quantity of Merrifield's peptide resin (10 g) was weighed, vacuum pumped for an hour to remove any moisture or oxygen, and then suspended in 100 ml of dry, degassed THF. (Merrifield's peptide resin is a chloromethylated divinyl benzene-polystyrene copolymer, this particular version having 2% cross-linking, and containing approximately 1 milliequivalent of chlorine per gram of resin. It was used in the form of 200–400 mesh beads, and is available from Aldrich Chemical Company of Milwaukee, Wis.). This polymer suspension was cooled to −100° C. and then treated with the monometallated primary phosphine solution, which had also been cooled to −100° C. The mixture was allowed to warm to room temperature and stirred for 48 hours until complete reaction was evidenced by the loss of yellow color in the solution.

Next, the supernatant THF was removed by canulla filtration. The beads were washed five times with 50 ml portions of THF. The fifth washing was free of chloride ion.

The beads were then resuspended in 100 ml of THF and were cooled to −100° C. They were next treated with a second equivalent of n-butyllithium in hexane (3.3 ml of a 3.0M solution; 10 mmols). The product of this reaction is a metallated secondary phosphine having the formula

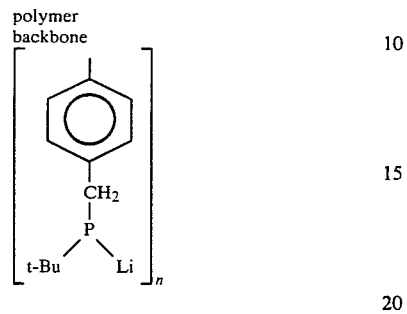

The beads were cooled once again, and a solution containing 2.46 grams (5 mmols) of [Rh(COD)Cl]$_2$ and 100 ml of THF was added to the reaction mixture. ("COD" is 1,5-cyclooctadiene.) The mixture was allowed to warm to room temperature and was stirred for 48 hours.

At the conclusion of that time, the beads were deep red. They were collected and washed as before until all evidence of halide was absent from the washings. The beads were then dried under a vacuum and stored in nitrogen at one atmosphere and −40° C.

EXAMPLE 2

A catalyst was synthesized using the general procedures described in Example 1, but using the transition metal complex [Rh(CO)$_2$Cl]$_2$ instead of the one used in Example 1. The amounts of reactants used were 1.7 ml of a 0.3M solution of LiPH(t—Bu) in THF, 0.5 g of the chlorinated polymer, 0.17 ml of a 2.9M solution of n-butyllithium in hexane, and 0.2 g of the rhodium complex, with 100 ml of THF as the reaction medium. The catalyst produced had the formula

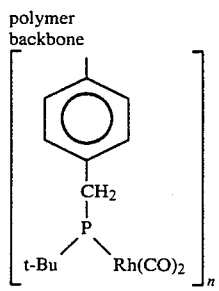

EXAMPLE 3

A third catalyst was synthesized using the general procedures discussed above, but using the transition metal complex Co(CO)$_4$I. The amounts of the various reactants used were 0.30 g of the complex, 0.122 ml of PH$_2$(t—Bu) (1 mmol), and 2 portions of 0.41 ml each of a 2.41M solution (1 mmol per aliquot) of n-butyllithium in hexane. The catalyst product that would result from this reaction has the formula

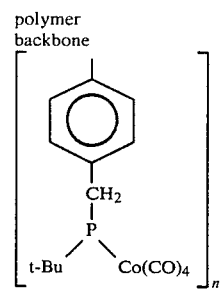

EXAMPLE 4

A catalyst having the formula

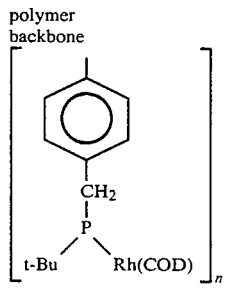

in the form of 200–400 mesh beads was tested for its ability to hydrogenate benzene. It was placed in a 500 ml glass vessel already flushed with N$_2$. Dry, degassed benzene was added with a syringe. The vessel was sealed, evacuated, and then pressurized with H$_2$. In the first run, 2.04 ml of benzene was used with 0.172 g of catalyst, and the reaction temperature was maintained at 30° C. Table 1 shows the decrease in H$_2$ pressure as time progressed.

TABLE 1

| Elapsed time (min.) | $P_{H_2}$ (psig) |
|---|---|
| 0 | 51 |
| 15 | 51 |
| 90 | 49 |
| 150 | 48 |
| 180 | 47 |
| 755 | 28 |
| 975 | 26 |
| 1035 | 25 |
| 1095 | 22 |
| 1150 | 20 |
| 1320 | 18 |
| 1475 | 15 |

The second run used the same amount of catalyst with 1.93 ml of benzene, and was conducted at 45° C. Table 3 shows its results.

TABLE 2

| Elapsed time (min.) | $P_{H_2}$ (psig) |
|---|---|
| 0 | 50 |
| 30 | 49 |
| 60 | 47 |
| 90 | 45 |
| 155 | 40.5 |
| 260 | 29.5 |
| 300 | 27 |

As this data shows, the 15° C. increase in reaction temperature sharply increased the rate of H$_2$ uptake.

EXAMPLE 5

The same type of catalyst used in Example 4 was tested with benzene. Catalyst weighing 0.20 g was submerged in 10.0 ml of benzene, and the reaction was carried out at 30° C., under a constant pressure of hydrogen [1 atm]. Table 3 shows the hydrogen uptake during this test.

TABLE 3

| $H_2$ uptake (ml) | Time (min) |
|---|---|
| 0 | 0 |
| 1 | 4.6 |
| 2 | 7.3 |
| 3 | 10.4 |
| 4 | 12.8 |
| 5 | 15.2 |
| 6 | 17.6 |
| 7 | 19.8 |
| 8 | 22.2 |
| 9 | 24.4 |
| 10 | 26.6 |
| 11 | 28.8 |
| 12 | 31.2 |
| 13 | 33.5 |
| 14 | 35.9 |
| 15 | 38.5 |
| 16 | 41.1 |
| 17 | 44.0 |
| 18 | 47.0 |
| 19 | 50.7 |
| 20 | 55.4 |
| 21 | 60.2 |
| 22 | 66.3 |

The calculated average rate of reaction here was 2.05 ml $H_2$/(g of catalyst)(min).

EXAMPLE 6

The same catalyst used in Example 5 was tested once again with benzene, this time at 40° C. Ten ml of benzene and 0.2 g of catalyst were used under 1 atm of hydrogen. Table 4 shows the hydrogen uptake in this experiment.

TABLE 4

| $H_2$ uptake (ml) | Time (min) |
|---|---|
| 0 | 0 |
| 1 | 2.2 |
| 2 | 5.1 |
| 3 | 8.1 |
| 4 | 11.3 |
| 5 | 14.4 |
| 6 | 16.9 |
| 7 | 19.7 |
| 8 | 23.2 |
| 9 | 26.4 |
| 10 | 28.6 |
| 11 | 30.6 |
| 12 | 32.1 |
| 13 | 34.2 |
| 14 | 36.4 |
| 15 | 38.2 |
| 16 | 40.3 |
| 17 | 43.4 |
| 18 | 46.4 |
| 19 | 50.6 |
| 20 | 52.8 |
| 21 | 55.3 |
| 22 | 57.6 |
| 23 | 59.6 |
| 24 | 62.0 |

The rate of hydrogen uptake was 1.95 ml $H_2$/(g of catalyst(min).

EXAMPLE 7

A catalyst having the same formula as in Examples 4–6 was tested for its ability to hydrogenate benzene at 50° C. Catalyst beads totalling 0.20 g were suspended in 10.0 ml of benzene. The reaction temperature was maintained at 50° C., under a $H_2$ atmosphere whose pressure was 759.1 mm Hg. Table 5 shows the hydrogen uptake as time progressed.

TABLE 5

| $H_2$ uptake (ml) | Time (min.) |
|---|---|
| 0 | 0.0 |
| 1 | 1.35 |
| 2 | 2.70 |
| 3 | 3.95 |
| 4 | 5.27 |
| 5 | 6.45 |
| 6 | 7.85 |
| 7 | 9.05 |
| 8 | 10.23 |
| 9 | 11.38 |
| 10 | 12.62 |
| 11 | 13.80 |
| 12 | 15.02 |
| 13 | 16.30 |
| 14 | 17.42 |
| 15 | 18.68 |
| 16 | 20.02 |
| 17 | 21.22 |
| 18 | 22.45 |
| 19 | 23.65 |
| 20 | 24.83 |
| 21 | 25.98 |
| 22 | 27.20 |
| 23 | 28.35 |
| 24 | 29.58 |
| 25 | 30.92 |
| 26 | 32.22 |
| 27 | 33.38 |
| 28 | 34.60 |
| 29 | 35.78 |
| 30 | 36.97 |
| 31 | 38.18 |
| 32 | 39.32 |
| 33 | 40.48 |
| 34 | 41.77 |
| 35 | 42.97 |
| 36 | 44.25 |
| 37 | 45.43 |
| 38 | 46.62 |
| 39 | 47.97 |
| 40 | 49.20 |
| 41 | 50.38 |

If this data is plotted, a nearly linear rate of hydrogen uptake is indicated. The slope of the plotted curve is 2.04 ml $H_2$/(g catalyst)(min).

In this example, as well as examples 4, 5, and 6, G.C. analysis of the benzene showed it to contain cyclohexane as the only product of hydrogenation.

The catalyst beads were recovered and stored for approximately 3 weeks at room temperature in air. They were then placed in a glass vessel containing benzene. When pressurized with $H_2$, hydrogenation resumed. Ten repeated pressurizations all showed $H_2$ uptake, indicating good catalyst activity.

EXAMPLE 8

A catalyst having the same formula as in Examples 4–7 was tested for its ability to hydrogenate toluene at 46° C. Catalyst amounting to 0.20 g was used with 10.0 ml of toluene. Table 6 shows the hydrogen uptake as time progressed, under a total $H_2$ pressure of one atmosphere.

TABLE 6

| H₂ uptake (ml) | Elapsed time (min.) |
| --- | --- |
| 0 | 0 |
| 0.2 | 5 |
| 0.8 | 10 |
| 1.2 | 15 |
| 1.6 | 20 |
| 2.0 | 25 |
| 2.6 | 30 |
| 3.4 | 35 |
| 4.2 | 40 |
| 5.1 | 45 |
| 6.1 | 50 |
| 7.1 | 55 |
| 8.7 | 61 |
| 10.1 | 66 |
| 14.8 | 80 |
| 16.7 | 85 |
| 18.5 | 89 |
| 22.3 | 96 |
| 28.6 | 108 |

After 80 minutes the rate of hydrogen uptake was 2.22 ml H₂ per minute per gram of catalyst. G.C. analysis of the toluene showed it to contain methylcyclohexane as the only product of hydrogenation.

As the examples show, aromatic compounds can be hydrogenated under relatively mild conditions. Napthalene, acetonitrile, and nitrobenzene apparently will not hydrogenate with the catalysts described above under conditions as mild as in the examples.

The catalysts in the above examples have transition metals attached to phosphorus by a phosphido type linkage. This is the key point which distinguishes these compounds from prior art phosphine-linked catalysts. Although transition metal-phosphorus bonding in both the present invention and the prior art catalysts described is covalent, the sources of the bonding electrons can be considered to be different in the two cases. In the transition metal-phosphine covalent bond the two electrons of the metal-phosphorus bond can both be considered to originate from the phosphorus atom; i.e. a dative covalent bond. In the transition metal-phosphido bond of the present invention, both the metal and the phosphorus atom are considered to contribute one electron each to the bond. Therefore the phosphido unit can be considered an anionic ligand and the linkage to a transition metal will be considerably stronger. This will reduce the likelihood of metal loss under operating conditions.

Synthesis of catalysts in accordance with the present invention can readily be carried out in situ, either wholly or in part.

Catalysts in accordance with the present invention will generally be stable in the presence of water and some acids.

The preceding examples are intended to illustrate the present invention, and are not an exhaustive listing of all possible embodiments.

I claim:

1. A catalyst which has the formula

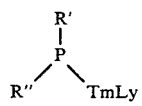

where

R′ and R″ are independently any organic or inorganic functionality capable of bonding to phosphorus;

Tm is a d-block transition metal; and

Ly is any functionality capable of bonding to a d-block transition metal.

2. The catalyst of claim 1, where R′ includes a polymeric material.

3. The catalyst of claim 2, where R″ is an aliphatic, alicyclic, or aromatic group.

4. The catalyst of claim 3, where Tm is selected from the group consisting of iron, cobalt, nickel, ruthenium, rhodium, palladium, osmium, iridium, and platinum.

5. The catalyst of claim 4, where R″ is an alkyl or aryl group.

6. The catalyst of claim 5, where the polymeric material of R′ has multiple sites available for the anchoring of metal complexes via phosphorus.

7. The catalyst of claim 6 where Ly is a halide, aliphatic, alicyclic, aromatic, phosphine, phosphate, phosphite, amine, thiol, sulfide, sulfate, or sulfite.

8. The catalyst of claim 7, where Ly is a diene, trialkyl or triaryl phosphine, or trialkyl or triaryl phosphite, carbon monoxide, or cyclopentadienyl group.

9. The catalyst of claim 8, where Tm is rhodium.

10. A catalyst which has the formula

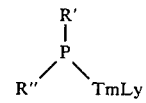

where

R′ is a methylated styrene-divinyl benzene copolymer;

R″ is an alkyl or aryl group;

Tm is selected from the group consisting of iron, cobalt, nickel, ruthenium, rhodium, palladium, osmium, iridium, and platinum; and Ly is any functionality capable of bonding to a d-block transition metal.

11. The catalyst of claim 10, where Ly is a diene, trialkyl or triaryl phosphine, trialkyl or triaryl phosphite, carbon monoxide, or cyclopentadienyl group.

12. The catalyst of claim 11, where R″ is t-butyl and Tm is rhodium.

13. A process for synthesizing a phosphido type transition metal catalyst, comprising the steps of:

(a) reacting a halogenated functionality capable of bonding to phosphorus with a monometallated primary phosphine to form a secondary phosphine;

(b) reacting the secondary phosphine with a metallated organic radical to deprotonate and metallate the secondary phosphine; and (c) reacting the metallated secondary phosphine with a transition metal compound having the formula XTmLy, where X is any inorganic, anionic functional group, Tm is a d-block transition metal, and Ly is any functional group capable of bonding to a d-block transition metal, to form a phosphido type linkage between the phosphorus and transition metal atoms.

14. The process of claim 13, where the steps are performed all or partially in situ.

15. The process of claim 13, where step (a) comprises reacting a polymeric material, which has multiple sites available for the anchoring of metal complexes via phosphorus, with a monometallated primary phosphine to form a secondary phosphine.

* * * * *